US009724400B2

(12) United States Patent
Daniell et al.

(10) Patent No.: US 9,724,400 B2
(45) Date of Patent: Aug. 8, 2017

(54) ADMINISTRATION OF PLANT EXPRESSED ORAL TOLERANCE AGENTS

(75) Inventors: Henry Daniell, Winter Park, FL (US); Roland Herzog, Gainesville, FL (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1166 days.

(21) Appl. No.: 13/508,754

(22) PCT Filed: Nov. 9, 2010

(86) PCT No.: PCT/US2010/055978
§ 371 (c)(1),
(2), (4) Date: Aug. 1, 2012

(87) PCT Pub. No.: WO2011/057243
PCT Pub. Date: May 12, 2011

(65) Prior Publication Data
US 2013/0007926 A1 Jan. 3, 2013

Related U.S. Application Data

(60) Provisional application No. 61/259,358, filed on Nov. 9, 2009.

(51) Int. Cl.
| | | |
|---|---|---|
| A61K 38/36 | (2006.01) |
| C12N 9/64 | (2006.01) |
| C12N 15/82 | (2006.01) |
| C12N 15/15 | (2006.01) |
| C07K 14/745 | (2006.01) |
| A61K 39/00 | (2006.01) |
| A61K 38/48 | (2006.01) |

(52) U.S. Cl.
CPC ...... *A61K 39/0008* (2013.01); *A61K 38/4846* (2013.01); *C12N 9/644* (2013.01); *C12N 15/8214* (2013.01); *C12N 15/8257* (2013.01); *C12Y 304/21022* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 5,693,507 | A | 12/1997 | Daniell |
| 5,877,402 | A | 3/1999 | Maliga |
| 5,932,479 | A | 8/1999 | Daniell |
| 6,642,053 | B1 | 11/2003 | Daniell |
| 6,680,426 | B2 | 1/2004 | Daniell |
| 7,129,391 | B1 | 10/2006 | Daniell |
| 7,135,620 | B2 | 11/2006 | Daniell |
| 7,294,506 | B2 | 11/2007 | Daniell |
| 7,354,760 | B2 | 4/2008 | Daniell |
| 2002/0053094 | A1 | 5/2002 | McBride et al. |
| 2002/0162135 | A1 | 10/2002 | Daniell |
| 2004/0177402 | A1 | 9/2004 | Daniell |
| 2005/0108792 | A1 | 5/2005 | Daniell |
| 2007/0124830 | A1 | 5/2007 | Daniell |
| 2007/0179095 | A1 | 8/2007 | Alpan et al. |
| 2008/0213222 | A1 | 9/2008 | High et al. |
| 2008/0241916 | A1 | 10/2008 | Daniell |
| 2008/0311139 | A1 | 12/2008 | Daniell |

FOREIGN PATENT DOCUMENTS

| | | |
|---|---|---|
| WO | 9910513 | 3/1999 |
| WO | 0164850 | 9/2001 |
| WO | 0164927 | 9/2001 |
| WO | 0164929 | 9/2001 |
| WO | 0172959 | 10/2001 |
| WO | 03057834 | 7/2003 |
| WO | 2004005467 | 1/2004 |
| WO | 2004005480 | 1/2004 |
| WO | 2004005521 | 1/2004 |
| WO | 2006027865 | 3/2006 |
| WO | 2007053183 | 10/2007 |
| WO | 2008121947 | 10/2008 |
| WO | 2008121953 | 10/2008 |
| WO | 2009058355 | 5/2009 |

OTHER PUBLICATIONS

Gao et al (Protein Expression and Purification, 37, pp. 89-96, 2004).*

(Continued)

*Primary Examiner* — Elizabeth McElwain
*Assistant Examiner* — Stephen Uyeno
(74) *Attorney, Agent, or Firm* — Kathleen D. Rigaut; Dann, Dorfman, Herrell and Skillman

(57) ABSTRACT

Protein replacement therapy for patients with hemophilia or other inherited protein deficiencies is often complicated by pathogenic antibody responses, including antibodies that neutralize the therapeutic protein or that predispose to potentially life-threatening anaphylactic reactions by formation of IgE. Using murine hemophilia B as a model, we have developed a prophylactic protocol against such responses that is non-invasive and does not include immune suppression or genetic manipulation of the patient's cells. Oral delivery of coagulation factor IX (F. IX) expressed in chloroplasts, bioencapsulated in plant cells, effectively blocked formation of inhibitory antibodies in protein replacement therapy. Inhibitor titers were mostly undetectable and up to 100-fold lower in treated mice when compared to controls. Moreover, this treatment eliminated fatal anaphylactic reactions that occurred after 4 to 6 exposures to intravenous F. IX protein. While only 20-25% of control animals survived after 6-8 F. IX doses, 90-95% of tolerized mice survived 12 injections without signs of allergy or anaphylaxis. This high-responder strain of hemophilia B mice represents the first hemophilic animal model to study anaphylactic reactions. The plant material was effective over a range of oral antigen doses (equivalent to 5-80 µg recombinant F.IX/kg), and controlled inhibitor formation and anaphylaxis long-term, up to 7 months. Oral antigen administration caused a deviant immune response that suppressed formation of IgE and inhibitory antibodies. This cost-effective and efficient approach to oral delivery of protein antigens to the gut should be applicable to several genetic diseases that are prone to pathogenic antibody responses during treatment.

3 Claims, 5 Drawing Sheets

(56) References Cited

OTHER PUBLICATIONS

Zhang et al (Biotechnol. Appl. Biochem. 48, pp. 101-107, 2007).*
Ruhlman et al (Plant Biotechnology Journal, 5, pp. 495-510, 2007).*
Herzog et al (Seminars in Thrombosis and Hemostasis, 2004, 30(2): 215-226).*
Dioun et al (Journal of Allergy and Clinical immunology, 1998, 102(1): 113-117).*
Daniell et al., Multigene engineering: dawn of an exciting new era in biotechnology, Curr Opin Biotechnol., 2002, 136-41, 13(2).
Daniell et al., Milestones in chloroplast genetic engineering: an environmentally friendly era in biotechnology, Trends Plant Sci., 2002, 84-91, 7(2).
Leelavathi et al., Chloroplast expression of His-tagged GUS-fusions: a general strategy to overproduce and purify foreign proteins using transplasmotic plants as bioreactors, Molecular Breeding, 2003, 49-58, 11.
Watson et al., Expression of Bacillus anthracis protective antigen in transgenic chloroplasts of tobacco, a non-food/feed crop, Vaccine, 2004, 4374-84, 22(31-32).
Kumar et al., Plastid-expressed betaine aldehyde dehydrogenase gene in carrot cultured cells, roots, and leaves confers enhanced salt tolerance, Plant Physiol., 2004, 2843-54, 136(1).
Kumar et al., Stable transformation of the cotton plastid genome and maternal inheritance of transgenes, Plant Mol Biol., 2004, 203-16, 56(2).
Quesada-Vargas et al., Characterization of heterologous multigene operons in transgenic chloroplasts: transcription, processing, and translation, Plant Physiol., 2005, 1746-62, 138(3).
Koya et al., Plant-based vaccine: mice immunized with chloroplast-derived anthrax protective antigen survive anthrax lethal toxin challenge, Infect Immun., 2005, 8266-74, 73(12).
Daniell et al., Breakthrough in chloroplast genetic engineering of agronomically important crops, Trends Biotechnol., 2005, 238-45, 23(5).
Limaye et al., Receptor-mediated oral delivery of a bioencapsulated green fluorescent protein expressed in transgenic chloroplasts into the mouse circulatory system, FASEB J., 2006, 959-61, 20(7).
Lee et al., Plastid transformation in the monocotyledonous cereal crop, rice (*Oryza sativa*) and transmission of transgenes to their progeny, Mol Cells., 2006, 401-10, 21(3).
Daniell et al., Chloroplast genetic engineering, Biotechnol J., 2006, 26-33, 1(1).
Verma et al., Chloroplast vector systems for biotechnology applications, Plant Physiol., 2007, 1129-43, 145(4).
Ruhlman et al., Expression of cholera toxin B-proinsulin fusion protein in lettuce and tobacco chloroplasts—oral administration protects against development of insulitis in non-obese diabetic mice, Plant Biotechnol J., 2007, 495-510, 5(4).
Daniell et al., Transgene containment by maternal inheritance: effective or elusive? Proc Natl Acad Sci U S A, 2007, 6879-80, 104(17).
Chebolu et al., Stable expression of Gal/GalNAc lectin of Entamoeba histolytica in transgenic chloroplasts and immunogenicity in mice towards vaccine development for amoebiasis, Plant Biotechnol J., 2007, 230-9, 5(2).
Daniell et al., The complete nucleotide sequence of the cassava (*Manihot esculenta*) chloroplast genome and the evolution of atpF in Malpighiales: RNA editing and multiple losses of a group II intron, Theor Appl Genet., 2008, 723-37, 116(5).
Arlen et al., Effective plague vaccination via oral delivery of plant cells expressing F1-V antigens in chloroplasts, Infect Immun., 2008, 3640-50, 76(8).
Davoodi-Semiromi et al., The green vaccine: A global strategy to combat infectious and autoimmune diseases, Hum Vaccin., 2009, 488-93, 5(7).
Daniell et al., Plant-made vaccine antigens and biopharmaceuticals, Trends Plant Sci., 2009, 669-79, 14(12).

* cited by examiner

ADMINISTRATION OF PLANT EXPRESSED ORAL TOLERANCE AGENTS

RELATED APPLICATIONS

This application claims priority to U.S. Ser. No. 61/259,358, filed Nov. 9, 2009, which is incorporated herein in its entirety.

GOVERNMENT INTEREST

This invention was made with government support under grant no. R01 GM063879 awarded by the National Institute of Health; under grant no. R21 HL089813 awarded by the National Institute of Health; and under grant no. R01 HL051390 awarded by the National Institute of Health. The government has certain rights in the invention.

INTRODUCTION

Current treatment of the X-linked bleeding disorder hemophilia is based on intravenous (IV) infusion of recombinant or plasma-derived coagulation factor VIII (hemophilia A) or factor IX (hemophilia B) concentrate. In a subset of patients, humoral immune responses to the functional protein develop and pose a serious complication for factor replacement therapy. In hemophilia A, formation of inhibitory antibodies ("inhibitors") directed against factor VIII (F.VIII), a helper T cell dependent response, occur in 20-30% of patients. In subjects with severe disease, i.e. patients with <1% of coagulation activity, the incidence is approximately 40% (1). There is much progress in the risk assessment of inhibitor formation in patients early in therapy, utilizing a combination of genotyping (e.g. determination of the underlying F.VIII mutation and polymorphisms in the promoters of the cytokine genes IL-10 and TNFα), family history of inhibitor formation, ethnicity, and intensity of early treatment (2). Inhibitors increase the risk for bleeding-related morbidity and mortality. High-titer inhibitors (>5 Bethesda units, BU) prevent treatment with clotting factor product. Bypass reagents, such as activated factor VII, are expensive and pose thrombotic risks. Inhibitors can be eliminated by Immune Tolerance Induction (ITI) protocols, which are based on frequent high dose infusion of factor for months to several years, and often require amounts of products exceeding $1,000,000.

While the overall incidence of inhibitors is lower in hemophilia B (1-4%), 9-23% of patients with severe disease form inhibitors. These are typically high-titer and are almost exclusively confined to subjects with gene deletions or early stop codons. A recent review calls for attention to this problem (3). ITI protocols are less effective for treatment of inhibitors to coagulation factor IX (F.IX). Importantly, studies found that up to 50% of patients with F.IX inhibitors may experience potentially life-threatening anaphylactic reactions to F.IX, which also preclude the subject from home treatment and severely hinder ITI protocols. These acute severe and systemic type I hypersensitive allergic reactions, often attributed to IgE formation, and have been reported for treatment of hemophilia A and B, lysosomal storage disorders (LSDs) such as Pompe and Fabry disease, and others (4-9). No prophylactic protocols are currently available for prevention of these pathogenic antibody responses.

DETAILED DESCRIPTION

Figure 1:
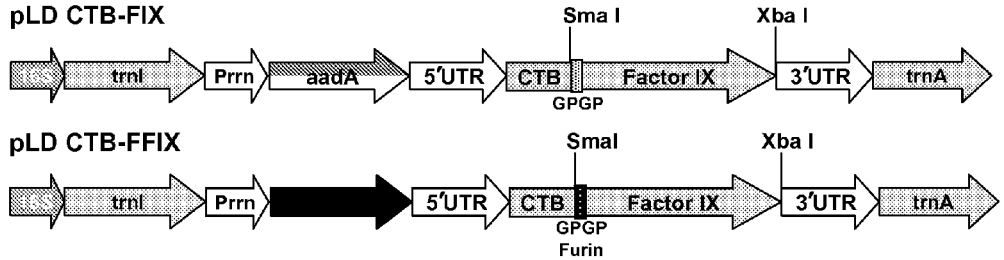
FIG. 1. Characterization of transplastomic plants (A) Schematic representation of chloroplast transformation vectors. Prrn, rRNA operon promoter; aadA, aminoglycoside 3'-adenylyltransferase gene; 5' UTR, promoter and 5' untranslated region of psbA gene; 3' UTR, 3' untranslated region of psbA gene. (B) Southern blot analysis. WT, Untransformed; 1-4, Transplastomic lines. (C) Western blot analysis of transplastomic lines expressing CTB-FIX and CTB-FFIX probed with CTB antibody and FIX antibody. WT, Untransformed plant extract; Y, M & O, Plant extract from young, mature and old transplastomic leaves. (D) Native PAGE. Total soluble protein extracted from transplastomic leaves, resolved by Native PAGE and probed with CTB antibody.
Figure 1:
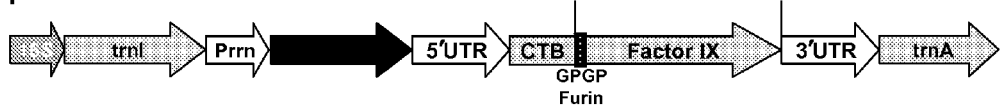
Figure 1:
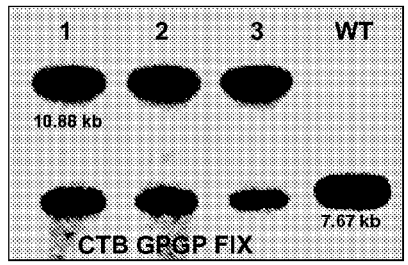
Figure 1:
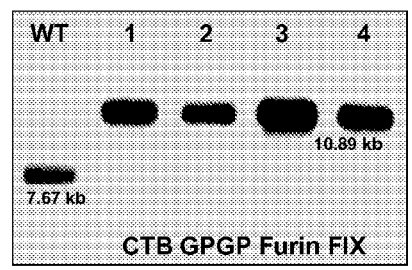
Figure 1:
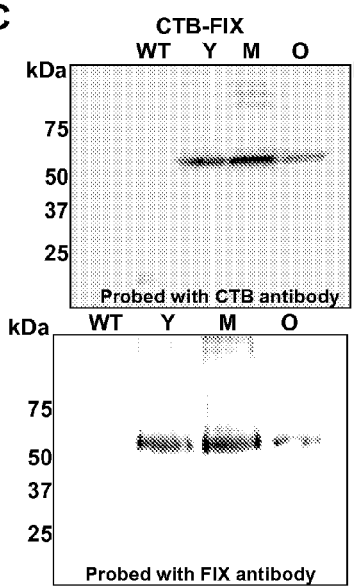
Figure 1:
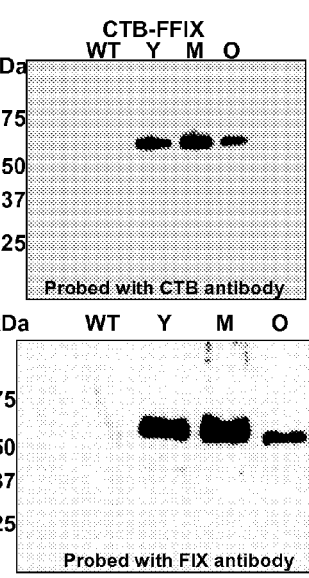
Figure 1:
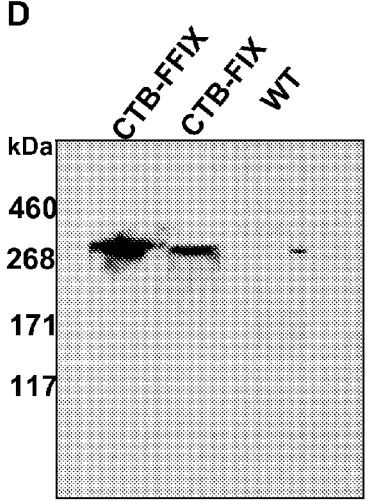

The inventors successfully demonstrate expression of coagulation factors in transgenic chloroplasts and also evaluation of induced tolerance to the same by oral administration of compositions comprising chloroplasts containing expressed factors. This is the first report of coagulation factor expression in any cellular compartment of transgenic plants. Based on the inventors' research, a new oral tolerance therapy is now possible that is used either prophylacticly or as a treatment to address sensitization to proteins utilized in protein replacement therapy. The methods and compositions disclosed herein may be used in conjunction with protein replacement therapy for diseases including, but not limited to, Hemophilia A, Hemophilia B, Pompe disease, Fabry disease, Gaucher disease, Mucopolysaccharidosis I, or Niemann-Pick disease.

Oral delivery of coagulation factors has long been discussed as a potential approach to tolerance induction in hemophilia (10). However, realization has been elusive, likely because of inefficient delivery of the antigen to the gut associated lymphoid tissue (GALT). The inventors sought to develop an alternative approach, using transplastomic technology as a means of efficient and potentially tolerogenic oral delivery of F.IX. There is concern that the prokaryotic nature of the chloroplast may not perform all of the post-translational modifications required to produce biologically active F.IX. Despite this concern, the inventors endeavored to determine whether delivery of the polypeptide to the GALT via bioencapsulation by the plant cell would result in tolergenic antigen presentation that modulates immune response upon intravenous administration of functional F.IX protein. Results demonstrate that repeated oral delivery of chloroplast-derived F.IX suppressed inhibitor development and prevented life-threatening anaphylactic reactions to F.IX replacement therapy in a murine model of hemophilia B.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

Methods, vectors, and compositions for transforming plants and plant cells are taught for example in WO 01/72959; WO 03/057834; and WO 04/005467. WO 01/64023 discusses use of marker free gene constructs.

Proteins expressed in accord with certain embodiments taught herein may be used in vivo by administration to a subject, human or animal, in a variety of ways. The pharmaceutical compositions may be administered orally or parenterally, i.e., subcutaneously, intramuscularly or intravenously. Thus, this invention provides compositions for parenteral administration which comprise a solution of the fusion protein (or derivative thereof) or a cocktail thereof dissolved in an acceptable carrier, preferably an aqueous carrier. A variety of aqueous carriers can be used, e.g., water, buffered water, 0.4% saline, 0.3% glycerine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of fusion protein (or portion thereof) in these formulations can vary widely depending on the specific amino acid sequence of the subject proteins and the desired biological activity, e.g., from less than about 0.5%, usually at or at least about 1% to as much as 15 or 20% by weight and will be selected primarily based on fluid volumes, viscosities, etc., in accordance with the particular mode of administration selected.

Therapeutic compositions produced by embodiments of the present invention can be administered by the consumption of the foodstuff that has been manufactured with the transgenic plant producing the therapeutic protein. The edible part of the plant is used as a dietary component while the therapeutic protein is administered in the process.

Thus, in one embodiment, the invention pertains to an administratable tolerance inducing composition that comprises an oral tolerance factor, such as an coagulation factor, having been expressed by a plant and a plant remnant. A plant remnant may include one or more molecules (such as, but not limited to, proteins and fragrments thereof, minerals, nucleotides and fragments thereof, plant structural components (such as cellular compartments), etc.) derived from the plant in which the antigen was expressed. Accordingly, a vaccine pertaining to whole plant material (e.g., whole or portions of plant leafs, stems, fruit, etc.) or crude plant extract would certainly contain a high concentration of plant remnants, as well as a composition comprising purified antigen that and one or more detectable plant remnant.

The tolerance inducing compositions of certain embodiments of the present invention may be formulated with a pharmaceutical vehicle or diluent for oral, intravenous, subcutaneous, intranasal, intrabronchial or rectal administration. The pharmaceutical composition can be formulated in a classical manner using solid or liquid vehicles, diluents and additives appropriate to the desired mode of administration. Orally, the composition can be administered in the form of tablets, capsules, granules, powders and the like with at least one vehicle, e.g., starch, calcium carbonate, sucrose, lactose, gelatin, etc. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol or the like and combination thereof. In addition, if desired, the vaccine may contain minor amounts of auxiliary substances such as wetting or emulsifying agents, pH buffering agents, or adjuvants which enhance the effectiveness of the vaccines. The preparation for parental administration includes sterilized water, suspension, emulsion, and suppositories. For the emulsifying agents, propylene glycol, polyethylene glycol, olive oil, ethyloleate, etc. may be used. For suppositories, traditional binders and carriers may include polyalkene glycol, triglyceride, witepsol, macrogol, tween 61, cocoa butter, glycerogelatin, etc. In addition, pharmaceutical grades of mannitol, lactose, starch, magnesium stearate, sodium saccharine, cellulose, magnesium carbonate and the like can be used as excipients.

Oral tolerance factors may be administered by the consumption of the foodstuff that has been manufactured with the transgenic plant and the edible part of the plant expressing the antigen is used directly as a dietary component while the vaccine is administrated in the process.

The tolerance inducing proteins may be provided with the juice of the transgenic plants for the convenience of administration. For said purpose, the plants to be transformed are preferably selected from the edible plants consisting of tomato, carrot and apple, which are consumed usually in the form of juice.

Those skilled in the art will appreciate that active variants of the genes specifically disclosed herein may be employed to produce plant derived therapeutic compositions. J Exp Med. 1997 May 19; 185(10):1793-801 provides some specific examples of fragments of known antigenic proteins and genes coding therefor.

According to another embodiment, the subject invention pertains to a transformed chloroplast genome that has been transformed with a vector comprising a heterologous gene that expresses a coagulation factor. In a related embodiment, the subject invention pertains to a plant comprising at least one cell transformed to express a coagulation factor.

In one embodiment, coagulation factor polypeptides according to the invention comprise at least 12, 15, 25, 50, 75, 100, 125, 150, 175, 200, 225, 250 or 265 contiguous amino acids selected from the amino acid sequence shown in SEQ ID NO: 2, or a biologically active variant thereof, as defined below. A coagulation factor polypeptide of the invention therefore can be a portion of a coagulation factor, a full-length coagulation factor protein, or a fusion protein comprising all or a portion of coagulation factor protein. Those skilled in the art, equipped with the teachings herein, will be enabled to express and utilize other known coagulation factors. Examples of other coagulation factors that may be used with the present invention include, but are not limited to, those polypeptide sequences associated with the following accession nos. NG_009258.1; NG_008953.1; NG_008107.1; NG_008051.1; NM_001993.3 and NM_00128.3, as provided in the related databases as of the filing date of the present invention. Also, Appendix A shows representative examples of sequences relating to noted coagulation factors. The interactive regions and protease regions of these sequences are known.

Coagulation factor polypeptide variants which are biologically active, i.e., confer an ability to increase tolerance against the corresponding factor upon oral administration— also are considered coagulation factor polypeptides for purposes of this application. Preferably, naturally or non-naturally occurring coagulation factor polypeptide variants have amino acid sequences which are at least about 55, 60, 65, or 70, preferably about 75, 80, 85, 90, 96, 96, or 98% identical to the amino acid sequence shown in SEQ ID NO: 2 or a fragment thereof. Percent identity between a putative coagulation factor polypeptide variant and an amino acid sequence of SEQ ID NO: 2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an coagulation factor polypeptide can be found using computer programs well known in the art, such as DNASTAR software. Whether an amino acid change results in a biologically active coagulation factor polypeptide can readily be determined by assaying for coagulation factor activity, as described for example, in the specific Examples, below.

A coagulation factor polynucleotide can be single- or double-stranded and comprises a coding sequence or the complement of a coding sequence for an coagulation factor polypeptide. A coding sequence for coagulation factor polypeptide of SEQ ID NO: 2 is shown in SEQ ID NO: 1. Examples of other coagulation factor polynucleotides that may be used with the present invention include, but are not limited to, those polynucleotide sequences associated with the following accession nos. NG_009258.1; NG_008953.1; NG_008107.1; NG_008051.1; NM_001993.3 and NM_00128.3, as provided in the related databases as of the filing date of the present invention.

Degenerate nucleotide sequences encoding coagulation factor polypeptides, as well as homologous nucleotide sequences which are at least about 50, 55, 60, 65, 60, preferably about 75, 90, 96, or 98% identical to the nucleotide sequence shown in SEQ ID NO: 1 also are coagulation factor polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of coagulation factor polynucleotides which encode biologically active coagulation factor polypeptides also are coagulation factor polynucleotides.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

TABLE 2

Amino Acid Substitutions
Original Residue Exemplary Conservative
Substitutions, others are known in the art.

Ala; ser
Arg; lys, gln
Asn; gln; his
Asp; glu
Cys; ser
Gln; asn, lys
Glu; asp
Gly; pro
His; asn; gln
Ile; leu; val
Leu; ile; val
Lys; arg; gln
Met; leu; ile
Phe; met; leu; tyr
Ser; thr
Thr; ser
Trp; tyr
Tyr; trp; phe
Val; ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Variants and homologs of the coagulation factor polynucleotides described above also are coagulation factor polynucleotides. Typically, homologous coagulation factor polynucleotide sequences can be identified by hybridization of candidate polynucleotides to known coagulation factor polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the coagulation factor polynucleotides disclosed herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Variants of coagulation factor polynucleotides or polynucleotides of other species can therefore be identified by hybridizing a putative homologous coagulation factor polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to coagulation factor polynucleotides or their complements following stringent hybridization and/or wash conditions also are coagulation factor polynucleotides. Stringent wash conditions are well known and understood in the art and are disclosed, for example, in Sambrook et al., MOLECULAR CLONING: A LABORATORY MANUAL, 2$^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between an coagulation factor polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m=81.5° C.-16.6(\log_{10}[Na^+])+0.41(\% G+C)-0.63(\% \text{ formamide})-600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

In alternative embodiments, the invention pertains to a method of treating a subject having a genetic disease prone and at risk to experiencing an anaphylactic reaction responsive to protein replacement therapy. The method comprises subjecting the subject to an effective amount of a composition comprising a tolerance factor and a plant remnant, and administering a therapeutically effective amount of a protein corresponding to a defect or deficiency associated with said disease. Typically, a tolerance factor pertains to a coagulation factor (see above), an acid α-glucosidase (accession nos. NM_001079803.1, NM_001079804.1, NM_0001152.3), α-galactosidase A, (accession no. NM_000169.2) Glucocerebrosidase (accession nos. J03059, J03060), α-L-iduronidase (accession no. NM_000203.3), or sphingomyelinase (accession nos. NM_000543.3, NM_001007593.1. The principles described above with respect to coagulation factor polypeptides and polynucleotides and variants in the preceding eleven paragraphs also apply to the sequences associated with the accession nos. provided in this paragraph. Also, the disease treated typically pertains to Hemophilia A, Hemophilia B, Pompe disease, Fabry disease, Gaucher disease, Mucopolysaccharidosis I, or Niemann-Pick disease. The tolerance factors may be conjugated to a CTB protein (see, e.g., Lai, C Y, Journal of Biological Chemistry, (1977) 252:7249-7256, or accession no. DQ523223, also see ref 39) to enhance oral tolerance potential.

EXAMPLES

Example 1: Construction of Chloroplast Transformation Vector

Both chloroplast vectors pLD CTB-FIX and pLD CTB-FFIX (FIG. 1A) used in this study are based on the universal chloroplast vector pLD-Ctv that targets the expression cassette into the spacer region between the trnI and trnA genes of the chloroplast genome for integration via homologous recombination (19). In the CTB-FIX construct, a glycine-proline-glycine-proline (GPGP) hinge was created between the fusion elements to prevent steric hindrance whereas in the CTB-FFIX construct, along with the GPGP hinge, a furin cleavage site was also introduced. The CTB-FIX and CTB-FFIX fusion genes were regulated by the psbA promoter and 5' untranslated region (UTR) in order to achieve hyperexpression, as demonstrated previously for several other transgenes (20). The psbA 3' UTR placed at the 3' end of the fusion gene imparted transcript stability. The aadA gene driven by the tobacco plastid ribosomal operon promoter (Prrn) and the GGAGG ribosome binding site conferring spectinomycin resistance was utilized for selection.

Example 2: Regeneration of Transplastomic Plants and Evaluation of Transgene Integration by Southern Blot Analysis Transplastomic tobacco plants were produced as described earlier (12, 21). Chloroplast transgenic lines were examined by Southern blots in order to confirm site-specific transgene integration and to determine homoplasmy or heteroplasmy. Digestion of total plant DNA from untransformed plants (WT) with HindIII generated a 7.67 kbp fragment when hybridized with the [$^{32}$P]-labeled trnI-trnA flanking sequence probe indicating no integration of foreign DNA (FIG. 1B). All CTB-FIX transplastomic lines showed both 10.88 kb and 7.67 kb fragments, indicating heteroplasmy, whereas all CTB-FFIX transgenic lines showed only 10.89 kb fragment, indicating homoplasmy. Southern blots confirm site specific integration of the transgenes into the spacer region between the trnI and trnA genes (FIG. 1B). Homoplasmy in CTB-FIX transgenic lines was not achieved even after additional rounds of selection. This may be due to toxicity created by improperly folded FIX due to steric hindrance in the absence of a furin cleavage site (GPGP alone was inadequate to prevent steric hindrance). Transplastomic lines with roots were transferred to jiffy pellets and kept under high humidity initially for 2 weeks in a growth chamber, before plants were moved to the greenhouse.

Figure 2:
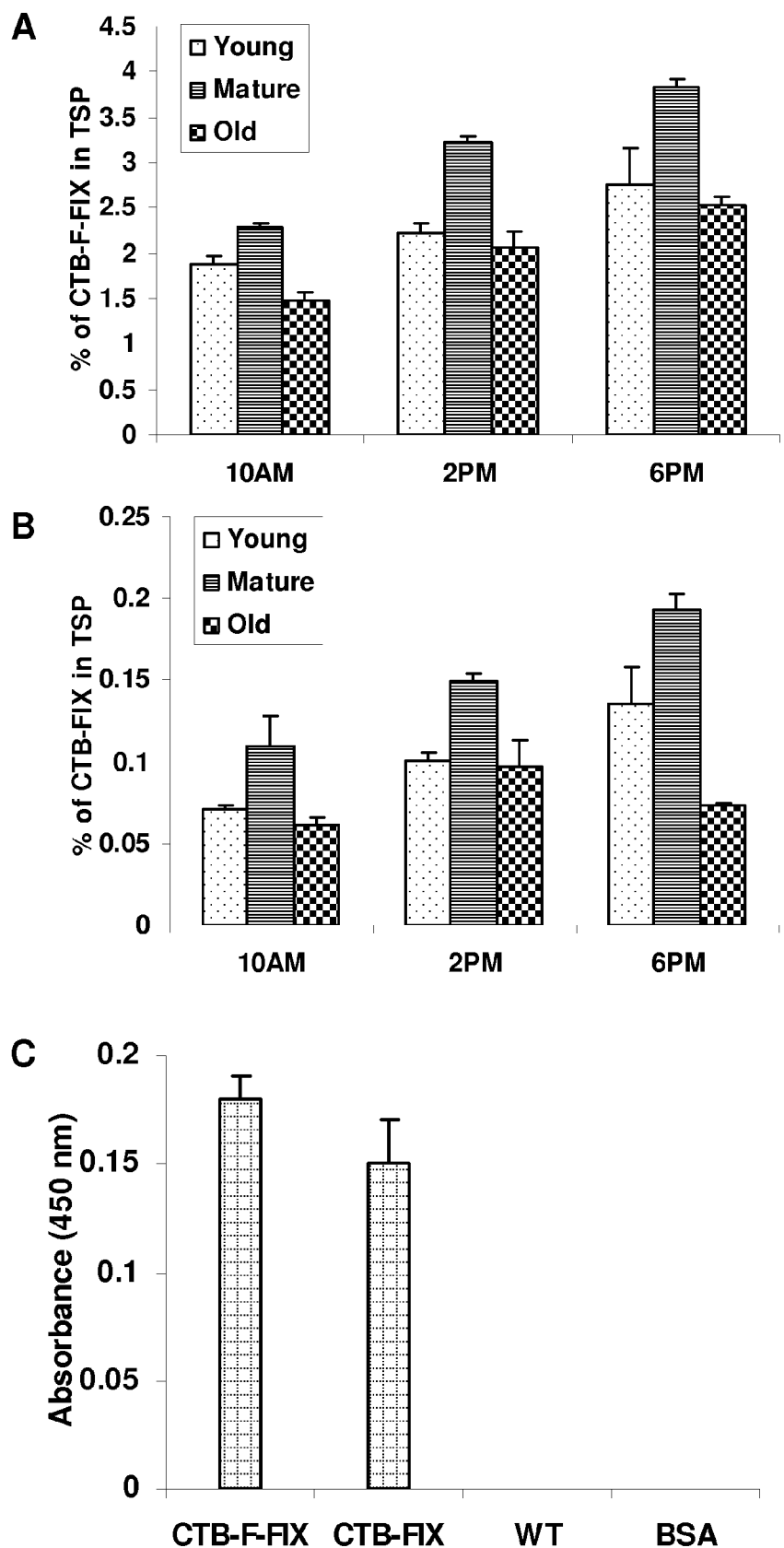
FIG. 2. Protein analysis in transplastomic tobacco plants. (A) & (B) Accumulation of CTB-FIX and CTB-FFIX as a function of light and developmental stage. (C) GM1 binding assay of CTB-FIX and CTB-FFIX tobacco transformants; WT, untransformed; BSA, negative control.

Example 3: CTB-FIX and CTB-FFIX Expression and Pentamer Assembly in Transgenic Tobacco Immunoblots probed with the CTB antibody showed the presence of a ~58-kDa fusion protein in both CTB-FIX and CTB-FFIX transplastomic lines (FIG. 1C). A similar banding pattern was observed by immunodetection with FIX antibody (FIG. 1C). Pentamer formation was observed in the native PAGE using CTB primary antibody (FIG. 1D). Quantitation of the fusion protein was carried out by densitometry on western blots of plant samples using known amounts of purified CTB. The expression levels varied significantly depending on the developmental stages and time of leaf harvest (FIG. 2A, 2B). Maximum expression was observed in mature leaves harvested at 6 PM. Transplastomic lines of CTB-FIX and CTB-FFIX had expression levels of up to 0.28% and 3.8% fusion protein respectively in the total soluble protein. Introduction of the furin cleavage site clearly stabilized FIX and enhanced its accumulation. The $GM_1$ binding assay demonstrated that pentameric structures of CTB-FIX and CTB-FFIX fusion proteins were formed within chloroplasts (FIG. 2C). This assay along with native PAGE confirmed the correct folding and disulfide bond formation of CTB pentamers within transgenic chloroplasts, as only the pentameric structure of CTB has the ability to bind to the $GM_1$ receptor (22).

Figure 3:
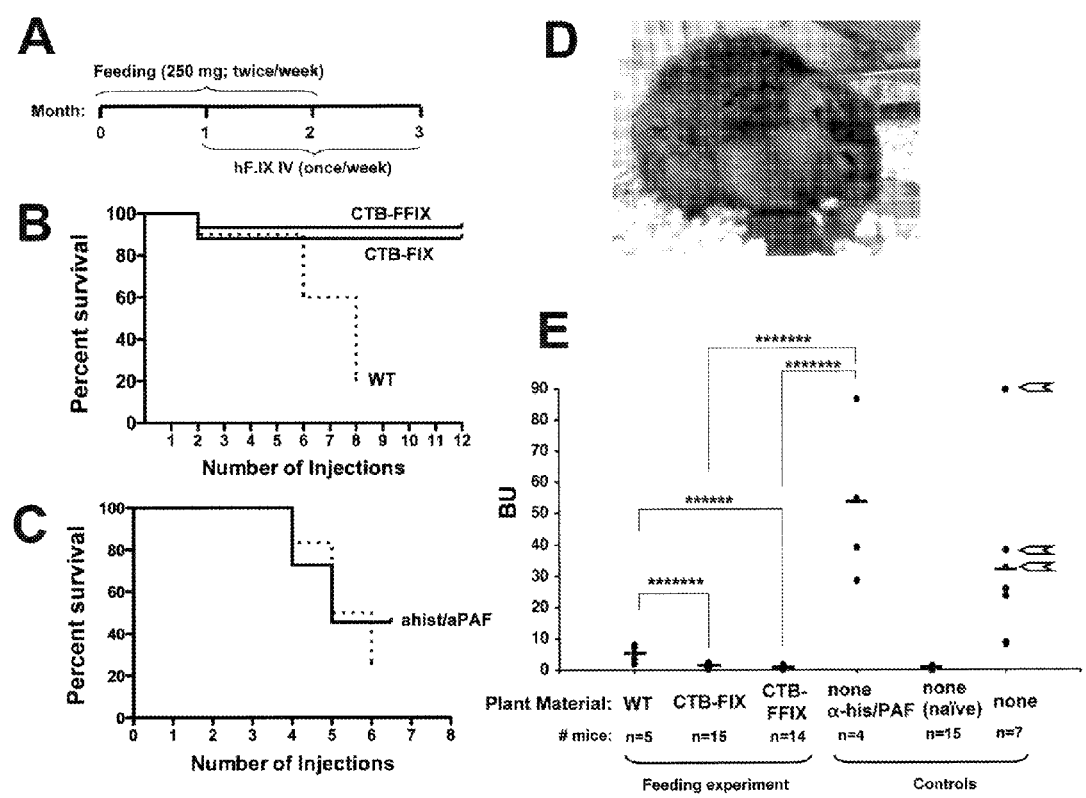
FIG. 3. Prevention of inhibitor formation and of anaphylactic reactions against intravenous hF.IX by oral administration of hF.IX chloroplast transgenic plant material in hemophilia B mice. (A) Feeding and hF.IX administration schedule. (B) Survival of mice fed with WT (n=10 mice at the onset of protein therapy), CTB-FIX (n=17), or CTB-FFIX (n=15) plant material as a function of the number of IV injections of hF.IX protein. (C) Survival of two control groups of unfed mice (starting with n=11, solid line, and n=12 mice, dotted line). Mice of one cohort (solid line) that survived 5 injections (n=5) received anti-histamine/anti-PAF prior to a $6^{th}$ injection of hF.IX ("ahist/aPAF"), resulting in 100%% survival. (D) Example of an allergic reaction preceding fatal anaphylactic shock in a control mouse after IV injection of hF.IX. The animal is in a hunched position and shows piloerection. (E) Inhibitor titers (in BU) at 3-month time point in WT, CTB, and CTB-FFIX fed mice (i.e. after 8 weekly IV injections of hF.IX). For comparison, titers in unfed control mice are shown that received anti-histamine/anti-PAF prior to a $6^{th}$ injection of hF.IX, or that were naïve, or that received 4 hF.IX administrations. For the latter, arrows indicate animals that died after a subsequent $5^{th}$ injection. Each dot represents an individual animal. Horizontal bars indicate average titers for each experimental group.

Example 4: Oral Delivery of F.IX Transplastomic Leaves Suppresses Inhibitor Formation and Fatal Anaphylaxis in Hemophilia B Mice Hemophilia B mice with targeted F9 gene deletion on C3H/HeJ genetic background form robust immune responses to human F.IX (hF.IX) upon protein or gene therapy (23). Therefore, three experimental groups received oral gavage of frozen powdered leaves (250 mg/dose), twice per week for 2 months, using leaves from untransformed (WT), CTB-FIX, or CTB-FFIX transplastomic plants (representing the equivalent of 0, 0.14, and 2 μg of recombinant hF.IX/dose/mouse, respectively). After 1 month, a therapeutic dose of recombinant hF.IX was given intravenously (IV) once per week (1 IU per mouse) for 2 months, i.e. extending 1 month beyond the feeding protocol (FIG. 3A). Two more groups received IV injections of hF.IX only, without feeding.

In unfed animals (n=11), severe allergic reactions were observed starting with the $4^{th}$ IV injection of hF.IX, at which time fatal anaphylactic reactions started to occur, and continued subsequently with an incidence of 20-40% (FIG. 3C). Similarly, 20-30% of WT fed mice (n=10) showed severe allergic reactions immediately following the $4^{th}$ and $5^{th}$ injection, including hunched position, piloerection, slowing of movement, tachypnea, and bronchospasms (example shown in FIG. 3D). During subsequent injections, ~50% of the mice had such reactions. Moreover, starting from the $6^{th}$ injection, ≥30% of animals died within 30 min to several hrs after IV injection of hF.IX, apparently from respiratory arrest (FIG. 3B). We were able to collect blood samples from 5 remaining mice immediately after the $8^{th}$ IV injection; within 2 hrs after which 3 additional mice died. In any case, 75-80% of mice treated with hF.IX were lost within 6-8 weekly injections (FIG. 3B, 3C), unless anti-anaphylactic drugs were given (see below).

In contrast, ≥90% of CTB-FIX or CTB-FFIX fed mice (n≥14 per cohort) survived the initial two-month period of 8 weekly hF.IX injections and even subsequent injections (total of 12 exposures; FIG. 3B). In none of these mice, we observed signs of allergic or anaphylactic reactions. Bethesda assays showed nearly complete to complete suppression of inhibitor formation in mice fed with CTB-FIX (1±0.5 BU) or CTB-FFIX (0.7±0.3 BU) as compared to inhibitor formation in antigen naïve hemophilia B mice (0.5±0.3 BU). Surviving WT-fed and unfed mice had significantly higher inhibitor titers, ranging from 2 to 10 BU (FIG. 3E).

We suspected that these data underrepresented protein therapy-induced inhibitor titers in these control groups, because those mice with fatal hypersensitive responses likely had stronger immune responses. To address these points, we first analyzed plasma obtained from unfed hemophilia B mice after 4 weekly hF.IX injections. These had substantially higher inhibitor titers of 8-90 BU (FIG. 3E), and the 3 of 7 mice with the highest titers died after the $5^{th}$ hF.IX administration (arrows in FIG. 3E). Second, 5 mice that had survived a $5^{th}$ injection received the $6^{th}$ dose of hF.IX under coverage with anti-histamine and anti-platelet activating factor (PAF). In this case, all 5 mice survived without allergic or anaphylactic response, and formed very high inhibitor titers of 29-87 BU (FIG. 3C, 3E).

Figure 4:
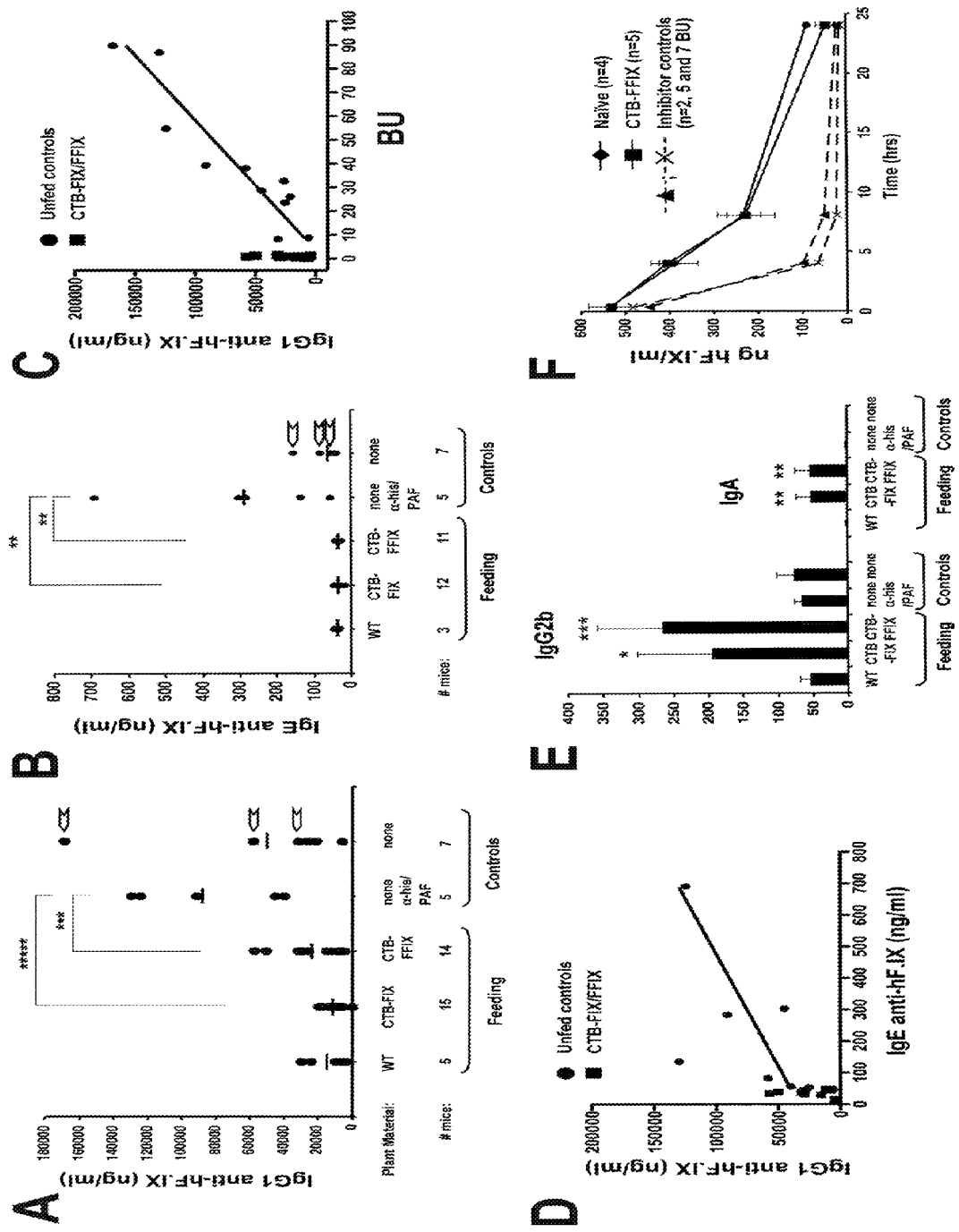
FIG. 4. Suppression of high-titer IgG and of IgE immunoglobulin responses directed against hF.IX. (A) IgG1 titers at 3-month time point in WT, CTB, and CTB-FFIX fed mice (i.e. after 8 weekly IV injections of hF.IX). Unfed control mice were as described in FIG. 3. (B) IgE titers for the same experimental groups. Arrows next to data point from unfed mice with 4 administrations of hF.IX protein indicate animals that died after a subsequent $5^{th}$ injection. (C) Correlation between IgG1 titers and inhibitor titers in unfed control mice (solid circles) and mice fed with CTB-FIX or CTB-FFIX (solid squares) plant material. (D) Correlation between IgG1 titers and IgE titers in unfed control mice (solid circles) and mice fed with CTB-FIX or CTB-FFIX (solid squares) plant material. (E) Immune deviation induced by oral administration. IgG2b and IgA titers are elevated in CTB-FIX and CTB-FFIX fed mice compared to WT fed and unfed control mice after repeated IV injection of hF.IX protein. (F) In comparison to naïve hemophilia B mice or CTB-FFIX fed mice, WT plant material fed mice with inhibitor development (shown are 2 individual mice with 5 and 7 BU, respectively) show enhanced clearance of IV injected hF.IX protein (1 IU/mouse). Shown are hF.IX antigen levels in plasma as a function of time after IV injection. Data point for naïve and CTB-FFIX fed mice are average ±SEM.

Example 5: Oral Administration of Bioencapsulated hF.IX Suppresses Formation of IgE and Inhibitors Via an Immune Deviation Mechanism Analysis of hF.IX-specific immunoglobulin formation showed that CTB-FIX/CTB-FFIX fed mice (and surviving WT fed mice) had average circulating IgG1 titers, which were significantly lower compared to control mice that were kept alive with anti-histamine/-PAF (FIG. 4A). While IgG1 titers in control mice correlated well with inhibitor titers, there was no correlation in CTB-FIX/CTB-FFIX fed mice, which therefore had formed non-inhibitory antibodies (FIG. 4C). Importantly, 3/7 control mice that had received 4 injections of hF.IX had detectable IgE titers, and titers of >50 ng/ml were predictive of subsequent fatal responses (FIG. 4B, arrows). Higher-titer IgE was found in 80% mice that had received a $6^{th}$ injection concomitant with anti-histamine/-PAF (FIG. 4B). These control mice showed a correlation between high-titer IgG1 (>40 μg/ml) and IgE formation, indicating that repeated IV administrations boosted Th2-driven antibody formation, resulting in activation of additional B cells with class switching to IgE (FIG. 4D). This correlation was not seen in CTB-FFIX fed mice, some of which developed IgG1 titers that would have been predicted to be associated with IgE (FIG. 4D). CTB-FIX/FFIX fed mice had IgE titers <40 ng/ml (the background of our assay) and no anaphylactic responses. Allergic reactions in rodents, while not previously identified in hemophilic mice, in general are caused by histamine and PAF release for IgE-dependent reaction, while an alternative, IgG dependent pathway has also been described, which, however, does not involve histamine (24). To address this point, additional control mice received hF.IX administration under coverage with anti-PAF alone (i.e. without anti-histamine), resulting in fatal anaphylaxis in all 3 animals tested, thereby further supporting an IgE-dependent mechanism in the hemophilia B mice.

None of WT fed or unfed mice formed IgG2a against hF.IX, thereby ruling out an IgG2a/complement dependent mechanism of anaphylactoid reactions. While IgG2a formation was highly variable and inconsistent in CTB-FIX/CTB-FFIX fed mice, tolerized mice consistently had circulating low-titers of TGF-β dependent antibodies, IgG2b and IgA, the hallmark subclass of a mucosal antibody response (FIG. 4E).

Feeding by CTB-FIX or CTB-FFIX material by itself did not result in a detectable systemic antibody response against hF.IX. The non-inhibitory antibodies in CTB-FFIX fed mice that formed upon protein therapy, in contrast to the inhibitors that developed in WT fed mice, did not cause enhanced clearance of IV infused hF.IX from the circulation (FIG. 4F).

Figure 5:
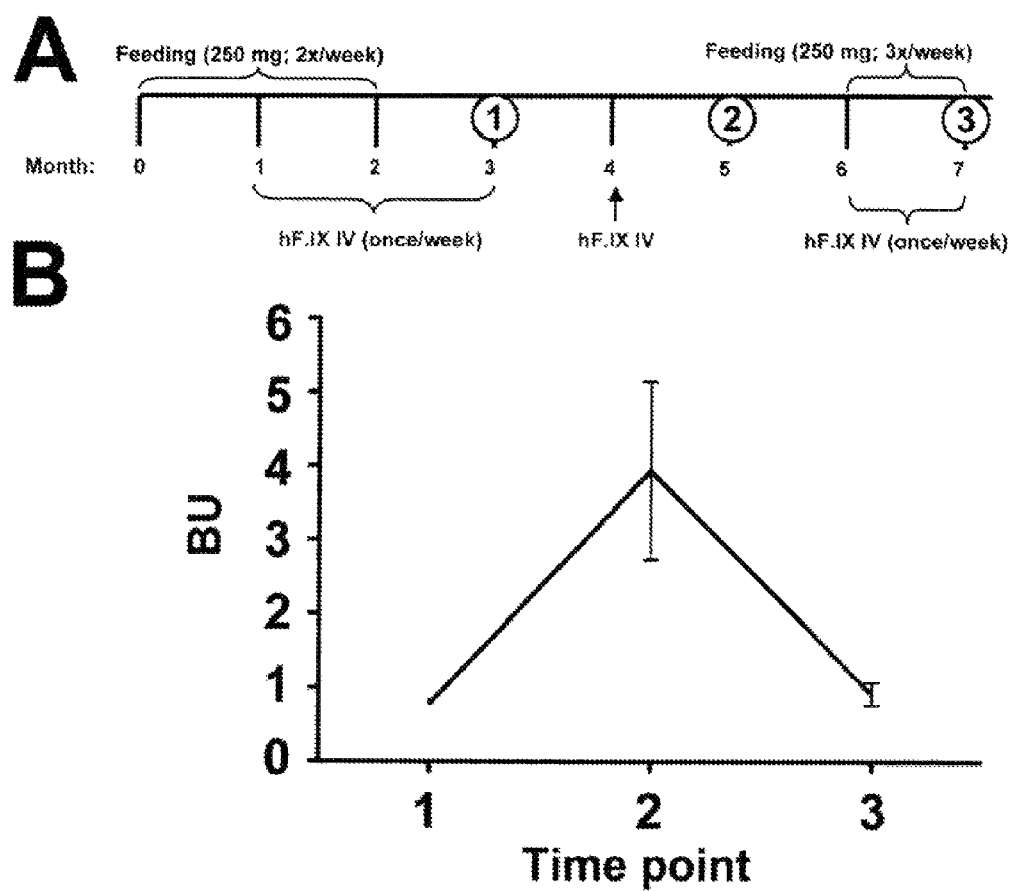
FIG. 5. Long-term control of inhibitor formation with bioencapsulated hF.IX. (A) Schedule of oral administration of CTB-FFIX plant material and IV injection of hF.IX protein. Numbers indicate time points of blood collection. (B) Average inhibitor titers (in BU ±SEM) at the indicated time points.

Example 6: Oral Administration of Bioencapsulated hF.IX can Control Inhibitor Formation Long-Term One month after the last hF.IX injection, one additional IV administration of hF.IX was performed in 9 CTB-FFIX fed mice (i.e. 2 months after the last feeding; FIG. 5A). This resulted in an increase of inhibitors to an average of 4 BU (FIG. 5B). Subsequently, treatment was resumed for 1 month (i.e. weekly IV infusions of hF.IX) while also continuing the feeding (3 oral gavages per week). At the end of this regimen, inhibitor titers had declined to baseline (FIG. 5B), indicating that the protocol can be used to control inhibitor formation long-term. Again, no allergic or anaphylactic responses were observed.

Discussion for Examples 1-6

Oral tolerance for hemophilia has been discussed for the past decade but has not been realized, in part because effective delivery of coagulation factor antigen to the gut has been challenging. A recent study concluded that the amount of coagulation factor required for feeding would be cost-prohibitive even for mouse experiments and therefore was not pursued (25). Here, we took advantage of an alternative technology that allows for efficient production, bioencapsulation and delivery of antigens to the GALT (14, 18, 26).

Human F.IX was produced at high level in plant chloroplasts as a fusion protein. The CTB fusion ensures stability of the transgenic protein in the chloroplast, and the nontoxic B subunit exhibits specific and high-affinity binding to the oligosaccharide domain of ganglioside GM1 (a lipid-based membrane receptor), thereby tethering the protein to the plasma membrane of host cells of the intestinal epithelium upon release from the plant cells in the ileum (18, 27).

Priming with CTB-FIX via an oral route reduced Th2-dependent antibody responses against intravenous hF.IX, and in particular protected from IgE formation, thereby eliminating allergic and anaphylactic reactions. Moreover, re-introduction of the antigen via the oral route successfully controlled inhibitor formation long-term without a need for immune suppressive drugs. Interestingly, plant materials expressing >10-fold different antigen levels were effective, which should facilitate clinical translation. The furin cleavage site, which directs release and exocytosis of the fused protein from gut epithelia, was not required for treatment but improved expression and accumulation of FIX in plant cells.

Repeated injections of hF.IX caused fatal reactions in most control animals, so that only mice survived that were either low responders or, possibly, spontaneously controlled the pathogenic antibody response. The magnitude of the antibody response was unmasked by pharmaceutical blockage of histamine release, thereby allowing animals to survive despite high production of IgE against hF.IX. Tests to detect IgE responses in patients with hemophilia are being refined (such as RAST, radioallergosorbent test) to improve safety of treatment. However, there are no protocols for preventing or suppressing IgE formation, nor has there been an animal model that mimics this aspect of hemophilia pathophysiology. Similar to observations in humans, the strain of mice we identified as prone to anaphylactic reactions has a F9 gene deletion (8). Symptoms in the mice are also very similar to IgE-mediated severe anaphylactic reactions observed in treatment of other genetic diseases, including hemophilia A and the LSDs Pompe disease (acid α-glucosidase deficiency) and Fabry disease (α-galactosidase A deficiency) (5-7, 28).

Protection of hemophilia B mice from inhibitor and IgE responses involved a deviant immune response, characterized by suppression of IgE and of high-titer IgG1, formation of non-neutralizing antibodies instead of inhibitors, and production of additional immunoglobulin subclasses (albeit at considerably lower titer in circulation compared to IgG1). Interestingly, presence of non-neutralizing antibodies has also been described in clinical ITI protocols (4). IL-4 production by CD4$^+$ T cells, i.e. by Th2 cells, promotes both IgG1 and IgE class switching. However, there is evidence that gut-associated regulatory T cells expressing IL-10 (such as Tr1 cells or IL-10$^+$ CD4$^+$CD25$^+$ Treg) can suppress IgE formation (29). Our findings on induction of IgG2b and IgA additionally suggest a role for the suppressive cytokine TGF-β, possibly derived from Th3 cells, in modulation of F.IX-specific B cell activation, which is consistent with the notion that the gut tissue has to control inflammatory responses to the large number of food-derived antigens it encounters daily.

Notably, the response to the allo- or autoantigen introduced to the GALT by oral administration of chloroplast transgenic plant material modulates responses to the antigen in other tissues, which we exploited to develop novel oral tolerance protocols. For instance, feeding of pro-insulin transgenic leaves suppressed destructive cellular immunity against pancreatic islet cells expressing the autoantigen (14). Here, we find that feeding hF.IX transgenic material controls pathogenic antibodies, such as inhibitory IgG1 and life-threatening IgE, that form upon IV administration of hF.IX protein concentrate.

The novel oral protocol described here offers several distinct advantages over other strategies. Alternative preclinical approaches for prophylactic tolerance induction to coagulation factors include gene transfer (e.g. to the liver, hematopoietic stem cells, or primary B cells) and transient immune suppressive regimens (30-34). Genetic manipulation poses risks of immunotoxicities and insertional mutagenesis; immune suppressive drugs have side effects, increase risk for opportunistic infections, and long-term consequences of use in pediatric patients are unclear. Administration of peptides to mucosal surfaces has also been described, which, however, is complicated in an outbred population because it requires knowledge of CD4$^+$ T cell epitopes, and may not be as effective (35).

The chloroplast system overcomes major limitations for protein production by elimination of the highly expensive fermentation and purification systems, cold storage, transportation and sterile injections. Site-specific integration into the chloroplast genome eliminates the concerns of position effect and gene silencing (12). Genetically modified chloroplast genomes of most crops are maternally inherited, and the absence of any reproductive structures offer efficient foreign gene containment (36) and therefore facilitate their safe production in the field (37). Plant cells provide bioencapsulation and protect therapeutic proteins from degradation in the stomach from acids and enzymes (26). Plants also reduce concerns about pathogen contamination as may be the case for production of proteins in transgenic animals. While these initial studies were carried out in non-food tobacco plants, lettuce chloroplast transformation system has been well developed for expression of human therapeutic proteins (14). We intend to develop hF.IX chloroplast transgenic lettuce for translational research.

With the recent development of novel enzyme replacement therapies for genetic diseases, such as for several LSDs, more reports are coming forward on immunotoxicities caused by protein infusion. Oral administration of transplastomic plant tissue provides a novel avenue for prevention and control of pathogenic antibody responses and anaphylactic reactions to systemically delivered therapeutic proteins in treatment of genetic diseases.

Materials and Methods for Examples 1-6
Vector Construction

Two CTB fusion constructs were made with human Factor IX (FIX). To prevent steric hindrance, a glycine-proline-glycine-proline (GPGP) hinge was introduced between the CTB and FIX in one of the construct. A furin cleavage site was also introduced along with GPGP hinge in the second construct. The cDNA sequence encoding F.IX was amplified using sequence specific restriction site flanking primers and cDNA clone of human factor IX as template. The PCR product was then cloned into the pCR BluntII Topo vector (Invitrogen) and the sequence was verified. Following SmaI/XbaI digestion, FIX gene was ligated into the pLD Ctv 5CP chloroplast transformation vector to create pLD-CTB FIX (only GPGP hinge between CTB and FIX) and pLD-CTB FFIX (with GPGP hinge and furin cleavage site between CTB and FIX) vectors (14).

Regeneration of Transplastomic Plants and Confirmation of Transgene Integration by Southern Blot Transplastomic plants using chloroplast expression vectors pLD CTB-FIX and pLD CTB-FFIX were regenerated as described elsewhere (12, 21). Total plant DNA (1 to 2 μg) isolated from leaves using Qiagen DNeasy plant mini kit was digested with HindIII, and Southern blot analysis was carried out to confirm integration and determine homoplasmy as described previously (38). Southern blots were hybridized with $^{32}P$ α[dCTP] labeled chloroplast flanking sequence probe (0.81 kb) containing the trnI-trnA genes. The transplastomic plants with roots were transferred to green house as described previously (12).

Immunoblot Analysis

Young, mature and old leaves from transformed plants raised in green house were collected at 10 AM, 2 PM and 6 PM, ground in liquid nitrogen to fine powder and stored at −80° C. Approximately 100 mg of pulverized leaf tissue was suspended in four volumes of protein extraction buffer (100 mM NaCl, 10 mM EDTA, 200 mM Tris-HCl pH 8, 0.05% Tween20, 100 mM DTT, 400 mM sucrose, 2 mM PMSF) and homogenized by vortexing for 20 min at 4° C. Total protein concentration was determined by Bradford protein assay reagent kit (Bio-Rad). Equal amounts of total protein along with known amount of purified bacterial CTB (Sigma, St. Louis, Mo.) were separated by SDS-PAGE and transferred to nitrocellulose membrane by electroblotting as described earlier (12, 35). To detect fusion proteins, blots were incubated with rabbit anti-CTB primary polyclonal antibody (1:3,000, Sigma) followed by HRP-conjugated donkey anti-rabbit secondary antibody (1:5,000, Southernbiotech, Birmingham, Ala.). The membrane was then incubated with SuperSignal® West Pico chemiluminescent substrate (Pierce, Rockford, Ill.) according to the manufacturer's instructions. Densitometric analysis of X-ray films for the fusion protein was carried out using Alphaimager® and AlphaEase FC software (Alpha Innotech, San Leandro, Calif.) by comparison with known quantities of standard. Fusion protein was also detected using goat anti human factor IX (1:3,000, Enzyme Research, South Bend, Ind.) antibody followed by donkey anti-goat IgG-HRP conjugated secondary antibody (1:5,000, Santa Cruz Biotechnology). Native-PAGE was also carried out and fusion protein was detected as described above. $GM_1$ receptor binding assays were performed as described previously (39).

Animal Experiments

Male C3H/HeJ mice with targeted deletion of the F9 gene (hemophilia B mice) were created as published (23, 31, 35). Animals were 8-10 weeks old at the onset of experiments. Plant leaf tissue was ground in liquid nitrogen and stored at −80° C. Prior to feeding, the material was re-suspended in sterile PBS. Oral gavage was performed using a 20 gauge stainless feeding needle (Popper and Sons, New York, N.Y.), while maintaining the animals under light anesthesia. Recombinant hF.IX (Benefix®) was injected into the tail vein at 1 IU per mouse. Plasma samples were collected by tail bleed into citrate buffer as described (23, 31, 35). For clearance studies, mice were bled from the retro-orbital plexus using heparinized micro-capillary tubes. To block anaphylactic reactions, 150 μg anti-histamine (triprolidine, Sigma) and 50 μg anti-platelet-activating factor (PAF) CV-3988 were co-injected IV (in 100 μl PBS) 5 min prior to administration of hF.IX (40).

Antigen and Antibody Measurements

Plasma levels of hF.IX antigen were measured by ELISA and inhibitory antibody titers determined by Bethesda assay as published (23). One Bethesda Unit (BU) represents the degree of inhibition that results in 50% residual coagulation activity. Immunocapture assay to determine titers of hF.IX-specific immunoglobulin subclasses were as described using IgA, IgE, IgG1, IgG2a, and IgG2b standards from Sigma. In order to measure IgE titers, IgG was removed from plasma samples using protein G agarose (Thermo Scientific—Pierce, Rockford, Ill.) prior to addition to microtiter plates coated with hF.IX protein. Statistical comparisons between experimental groups were assessed with unpaired student's T test. Differences were considered significant and reported with * for $P<0.05$,  for $P<0.01$, * for $P<0.001$, and so on.

REFERENCES

1. DiMichele D M (2006) Inhibitor treatment in haemophilias A and B: inhibitor diagnosis. *Haemophilia* 12 Suppl 6:37-41; discussion 41-42.
2. Ghosh K, Shetty S (2009) Immune response to FVIII in hemophilia A: an overview of risk factors. *Clin Rev Allergy Immunol* 37:58-66.
3. DiMichele D (2007) Inhibitor development in *haemophilia* B: an orphan disease in need of attention. *Br J Haematol* 138:305-315.
4. Franchini M, et al. (2009) Anaphylaxis in patients with congenital bleeding disorders and inhibitors. *Blood Coagul Fibrinolysis* 20:225-229.
5. Kadar J G, Schuster J, Hunzelmann N (2007) IgE-mediated anaphylactic reaction to purified and recombinant factor VIII in a patient with severe *haemophilia* A. *Haemophilia* 13:104-105.
6. Mohrenschlager M, Ollert M, Ring J (2008) A study on serum IgE and clinical symptomatology of atopy in patients suffering from the lysosomal storage disorder Fabry disease. *J Eur Acad Dermatol Venereol* 22:692-695.
7. Nicolino M, et al. (2009) Clinical outcomes after long-term treatment with alglucosidase alfa in infants and children with advanced Pompe disease. *Genet Med* 11:210-219.
8. Thorland E C, et al. (1999) Anaphylactic response to factor IX replacement therapy in *haemophilia* B patients: complete gene deletions confer the highest risk. *Haemophilia* 5:101-105.
9. Warrier I, et al. (1997) Factor IX inhibitors and anaphylaxis in hemophilia B. *J Pediatr Hematol Oncol* 19:23-27.
10. Terada K, Yagi Y, Niizuma T, Kataoka N (2001) Is oral tolerance therapy possible for *haemophilia* with inhibitors? *Vox Sang* 80:61-62.
11. Daniell H (2002) Molecular strategies for gene containment in transgenic crops. *Nat Biotechnol* 20:581-586.
12. Verma D, Samson N P, Koya V, Daniell H (2008) A protocol for expression of foreign genes in chloroplasts. *Nat Protoc* 3:739-758.
13. De Cosa B, Moar W, Lee S B, Miller M, Daniell H (2001) Overexpression of the Bt cry2Aa2 operon in chloroplasts leads to formation of insecticidal crystals. *Nat Biotechnol* 19:71-74.
14. Ruhlman T, Ahangari R, Devine A, Samsam M, Daniell H (2007) Expression of cholera toxin B-proinsulin fusion protein in lettuce and tobacco chloroplasts—oral administration protects against development of insulitis in non-obese diabetic mice. *Plant Biotechnol J* 5:495-510.
15. Oey M, Lohse M, Kreikemeyer B, Bock R (2009) Exhaustion of the chloroplast protein synthesis capacity by massive expression of a highly stable protein antibiotic. *Plant J* 57:436-445.
16. Davoodi-Semiromi A, Samson N, Daniell H (2009) The green vaccine: A global strategy to combat infectious and autoimmune diseases. *Hum Vaccin* 5:488-493
17. Daniell H, Singh N D, Mason H, Streatfield S J (2009) Plant-made vaccine antigens and biopharmaceuticals. *Trends Plant Sci* doi:10.1016/j.tplants.2009.09.009.
18. Limaye A, Koya V, Samsam M, Daniell H (2006) Receptor-mediated oral delivery of a bioencapsulated green fluorescent protein expressed in transgenic chloroplasts into the mouse circulatory system. *FASEB J* 20:959-961.
19. Daniell H, Datta R, Varma S, Gray S, Lee S B (1998) Containment of herbicide resistance through genetic engineering of the chloroplast genome. *Nat Biotechnol* 16:345-348.
20. Verma D, Daniell H (2007) Chloroplast vector systems for biotechnology applications. *Plant Physiol* 145:1129-1143.
21. Singh N D, Ding Y, Daniell H (2009) Chloroplast-derived vaccine antigens and biopharmaceuticals: protocols for expression, purification, or oral delivery and functional evaluation. *Methods Mol Biol* 483:163-192.
22. Merritt E A, et al. (1994) Crystal structure of cholera toxin B-pentamer bound to receptor GM1 pentasaccharide. *Protein Sci* 3:166-175.
23. Cao O, et al. (2009) Impact of the underlying mutation and the route of vector administration on immune responses to factor IX in gene therapy for hemophilia B. *Mol Ther* 17:1733-1742.
24. Finkelman F D (2007) Anaphylaxis: lessons from mouse models. *J Allergy Clin Immunol* 120:506-515; quiz 516-517.
25. Rawle F E, et al. (2006) Induction of partial immune tolerance to factor VIII through prior mucosal exposure to the factor VIII C2 domain. *J Thromb Haemost* 4:2172-2179.
26. Mason H S, Warzecha H, Mor T, Arntzen C J (2002) Edible plant vaccines: applications for prophylactic and therapeutic molecular medicine. *Trends Mol Med* 8:324-329
27. Haq T A, Mason H S, Clements J D, Arntzen C J (1995) Oral immunization with a recombinant bacterial antigen produced in transgenic plants. *Science* 268:714-716.
28. Sun B, et al. (2009) Immunomodulatory gene therapy prevents antibody formation and lethal hypersensitivity reactions in murine Pompe disease. *Mol Ther* doi: 10.1038/mt.2009.195.
29. von der Weid T, Bulliard C, Fritsche R (2001) Suppression of specific and bystander IgE responses in a mouse model of oral sensitization to beta-lactoglobulin. *Int Arch Allergy Immunol* 125:307-315.
30. Lei T C, Scott D W (2005) Induction of tolerance to factor VIII inhibitors by gene therapy with immunodominant A2 and C2 domains presented by B cells as Ig fusion proteins. *Blood* 105:4865-4870.
31. Mingozzi F, et al. (2003) Induction of immune tolerance to coagulation factor IX antigen by in vivo hepatic gene transfer. *J Clin Invest* 111:1347-1356.
32. Moayeri M, Hawley T S, Hawley R G (2005) Correction of murine hemophilia A by hematopoietic stem cell gene therapy. *Mol Ther* 12:1034-1042.
33. Nayak S, et al. (2009) Prophylactic immune tolerance induced by changing the ratio of antigen-specific effector to regulatory T cells. *J Thromb Haemost* 7:1523-1532.
34. Ponder K P (2008) Immune response hinders therapy for lysosomal storage diseases. *J Clin Invest* 118:2686-2689.
35. Cao O, et al. (2006) Immune deviation by mucosal antigen administration suppresses gene-transfer-induced inhibitor formation to factor IX. *Blood* 108:480-486.
36. Daniell H (2007) Transgene containment by maternal inheritance: Effective or elusive? *Proc Natl Acad Sci USA* 104:6879-6880.
37. Arlen P A, et al. (2007) Field production and functional evaluation of chloroplast-derived interferon-alpha2b. *Plant Biotechnol J* 5:511-525.
38. Kumar S, Daniell H (2004) Engineering the chloroplast genome for hyperexpression of human therapeutic proteins and vaccine antigens. *Methods Mol Biol* 267:365-383.
39. Daniell H, Lee S B, Panchal T, Wiebe P O (2001) Expression of the native cholera toxin B subunit gene and assembly as functional oligomers in transgenic tobacco chloroplasts. *J Mol Biol* 311:1001-1009.
40. Lu Y, et al. (2008) Human alpha 1-antitrypsin therapy induces fatal anaphylaxis in non-obese diabetic mice. *Clin Exp Immunol* 154:15-21.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. The teachings of all references cited herein, including patent-related references, are incorporated herein in their entirety to the extent not inconsistent with the teachings herein.

What is claimed is:

1. A method for suppressing coagulation factor inhibitor formation and IgE formation in response to an intravenously administered coagulation factor in a subject, the method comprising
expressing in a plant plastid a nucleic acid sequence encoding a coagulation factor polypeptide conjugated to cholera toxin b, and
orally administering to said subject a plant remnant comprising said plant plastid expressed coagulation factor conjugated to cholera toxin b, wherein said oral administration can be repeated as needed to control inhibitor formation.

2. The method of claim 1, wherein said coagulation factor polypeptide is Factor II, Factor III, Factor IV, Factor V, Factor VI, Factor VII, Factor VIII, Factor IX, Factor X, Factor XI, Factor XII, or Factor XIII.

3. A method for suppressing coagulation factor inhibitor formation and anaphylaxis in response to intravenous administration of Factor IX to a subject receiving Factor IX treatment, the method comprising expressing in a plant plastid a nucleic acid sequence encoding Factor IX conjugated to cholera toxin b, and orally administering to said subject a plant remnant comprising said plastid expressed Factor IX conjugated to cholera toxin b, wherein a systemic antibody response against Factor IX is not induced by said oral administration, and wherein said oral administration suppresses inhibitor formation and anaphylaxis in response to said intravenously administered Factor IX for up to 7 months.

* * * * *

UNITED STATES PATENT AND TRADEMARK OFFICE
CERTIFICATE OF CORRECTION

PATENT NO. : 9,724,400 B2
APPLICATION NO. : 13/508754
DATED : August 8, 2017
INVENTOR(S) : Henry Daniell and Roland Herzog Page 1 of 1

It is certified that error appears in the above-identified patent and that said Letters Patent is hereby corrected as shown below:

On the Title Page

Left-hand column, (73) Assignee, change Assignee to read:
The Trustees of the University of Pennsylvania, Philadelphia, PA
--University of Florida Research Foundation, Inc., Gainesville, FL--

Signed and Sealed this
Fifteenth Day of May, 2018

Andrei Iancu
*Director of the United States Patent and Trademark Office*